(12) United States Patent
Davis et al.

(10) Patent No.: US 6,313,646 B1
(45) Date of Patent: Nov. 6, 2001

(54) IN-SITU ELECTROCHEMICAL-BASED MOISTURE SENSOR FOR DETECTING MOISTURE IN COMPOSITE AND BONDED STRUCTURES

(75) Inventors: Guy D. Davis, Baltimore; Chester M. Dacres, Columbia, both of MD (US)

(73) Assignee: Dacco SCI, Inc., Columbia, MD (US)

( * ) Notice: Subject to any disclaimer, the term of this patent is extended or adjusted under 35 U.S.C. 154(b) by 0 days.

(21) Appl. No.: 09/240,658

(22) Filed: Feb. 2, 1999

(51) Int. Cl.⁷ .............................. G01R 27/26; G01F 1/64
(52) U.S. Cl. .................. 324/690; 324/664; 324/693; 205/77.5; 205/791; 204/404
(58) Field of Search ................................ 324/664, 693, 324/690, 71.2; 205/775.5, 776.5, 791; 204/404, 406

(56) References Cited

U.S. PATENT DOCUMENTS 5,479,104 * 12/1995 Cambell ............................ 324/690
5,859,537 * 1/1999 Davis et al. ....................... 324/693
6,054,038 * 4/2000 Davis et al. ..................... 205/776.5

* cited by examiner

*Primary Examiner*—Safet Metjahic
*Assistant Examiner*—Vincent Q Nguyen

(57) ABSTRACT

A hand-held or permanently attached corrosion sensor is described that uses electrochemical impedance spectroscopy (EIS, also known as AC impedance) to detect coating and structural degradation caused by excessive moisture uptake of coated and uncoated composite laminations or honeycomb or adhesively bonded structures. The hand-held sensor is pressed against the surface of the structure or specimen to be inspected. Alternatively, the sensor electrode may be permanently or temporarily attached. An EIS spectrum can then be obtained in the field or under arbitrary conditions and the degree of moisture uptake or coating or material degradation can be determined from the resultant spectrum. There are no restrictions on the configuration of the structure being inspected. The area of detection is controlled by controlling the extent and degree of wetness of the surface. A dry surface will provide a localized measurement; a wet surface will allow inspection of the wetted area.

2 Claims, 5 Drawing Sheets

IN-SITU ELECTROCHEMICAL-BASED MOISTURE SENSOR FOR DETECTING MOISTURE IN COMPOSITE AND BONDED STRUCTURES

BACKGROUND OF THE INVENTION

1. Field of the Invention

The present invention relates to a portable, hand-held and nondestructive moisture-sensing device, based on electrochemical impedance spectroscopy (EIS), for detecting moisture in graphite/epoxy, glass/polyamide, and other composites and adhesively bonded structures. Repair operations in composite laminations or honeycomb structures become difficult and time-consuming in the presence of moisture, even at moisture contents as low as 0.5%. If the moisture is not removed by slow heating or exposure to a dry atmosphere, steam formed at elevated curing temperatures can result in more extensive damage than existed before the repair attempt. Moisture in honeycomb structures can result in corrosion of the thin core material and loss of structural integrity; moisture in an adhesive can reduce the mechanical strength of the adhesive and reduce interfacial bonding, and allow corrosion on hydration of the substrate at the interface with the adhesive. Under these conditions, an in-situ corrosion sensor was adapted to detect moisture in composites and honeycomb or adhesively bonded structures, even at moisture contents as low as 0.5%. It detects moisture in graphite/epoxy/Nomex honeycomb structures and aluminum/epoxy/aluminum structures is applicable to other bonded structures, as well. Coupled with a commercial portable computer, the hand-held sensor is capable of detecting moisture in composite and bonded components of various structures, including, for example, the F/A-18, F-14, EA-6B, and V-22 aircraft and the Boeing 777 series, among others.

In particular, the present invention relates to a portable or permanently fixed moisture sensor which is utilized under field (actual, environmental or in situ) conditions in detecting moisture in composite laminations or honeycomb structures, as well as other bonded structures, thereby preventing the formation of steam, resulting in subsequent structural voids, delaminations and disbonds during repair operations. It can also warn of possible moisture-induced degradation resulting from hydration of aluminum bonding surfaces or corrosion of core material well before serious deterioration of the material or structure has occurred.

2. Prior Art

A major goal in the electrochemical field has long been to create a sensor which could be utilized in field or service conditions to detect moisture of composite laminations or honeycomb and adhesively bonded structures of any size, before significant degradation has occurred. Moisture concentrations less than 1% in the composite or in the adhesive between the composite and the core can cause significant structural damage. To compensate for the lack of real-time data, the prior art relied on the drying schedules for parts requiring repair to be conservatively set, in order to prevent the possibility of entrapped moisture, particularly in large parts. Drying temperature and time are based primarily on historical experience and success for each material system and component configuration, with a typical schedule of several days at 160–180° F. (ambient pressure). The general consensus has been that larger composite parts presented a greater risk, because it was difficult to ascertain adequate drying schedules or to prevent entrapped moisture.

The only prior art available to inspect high-performance moisture content of composites, such as those used in the aerospace industry, is a method which teaches monitoring of the humidity level of the drying air, much like the humidistat in an household clothes dryer. Other prior art technologies that have been utilized include thermography, x-ray and neutron radiography. Thermography appears useful in detecting, but not quantifying trapped moisture in honeycomb materials. X-ray and neutron radiography are both quite sensitive in detecting trapped moisture, but their safety restrictions, ease of use, and costs have been major deterrents to date. Furthermore, portability has been a previous disadvantage to these radioscopic techniques.

Other moisture sensors are currently commercially available. These are either grossly qualitative instruments or expensive laboratory contraptions not suited for the target application. Of those that have relevance, the principles of operation of the meters themselves tend to fall into 3 categories: conductance/capacitance, microwave and infrared absorption. Most commercial moisture meters seem to be directed at either the boating, wood products or the food (i.e., grain, cereal, etc.) industries and not at the high-performance, typically conductive composites or adhesive bonds.

Conductance and capacitance meters are used primarily by the boating industry. The pin-type detector measures dc resistance between two probes pressed into the composite. Because of the damage generated by the pins, this type of detector is generally limited to wood and masonry. The pad-type detector transmits and receives radio frequency signals and relies on water's higher dielectric constant compared to the glass reinforced plastic or air. It is not suited for graphite composites due to the electrical conductivity of the fibers and it is limited in the depth of material that it can inspect.

Microwave dielectric-based systems and infrared meters are research lab instruments not suited for field applications. The infrared systems require a small physical sample for evaluation.

By contrast to the prior art, the proposed moisture sensor is small, rugged, suitable for conductive and nonconductive composites and honeycomb and adhesively bonded structures, and does not require insertion into the structure or cause other damage.

Presently, there is no portable, hand-held or permanently attached, in situ and moisture-detecting and monitoring device for high-performance composite laminations, honeycomb or other bonded structures which can evaluate degradation on structures or material of any size, under in situ or actual conditions, as well as under aggressive corrosive conditions, and requires no permanent attachment.

SUMMARY OF THE INVENTION

The principal objective of the present invention is to provide a portable, hand-held, or permanently attached in situ moisture-detecting and monitoring device for composite laminations, honeycomb or other bonded structures which can evaluate degradation on structures or material of any size, under in situ or actual conditions, as well as under aggressive corrosive conditions. The present invention allows for broad applicability, flexibility in utilizing the sensor in various environments without structural compromise and/or the ability to inspect and evaluate moisture content and correlative degradation of the actual structure, regardless of its size. In order to address the problem of determining moisture content in composite and bonded materials, the Davis el aL In-situ corrosion sensor, U.S. Pat. No. 5,859,537 and U.S. patent application Ser. No. 09/093, 001, was adapted to monitor moisture in composites and adhesive bonds. This adaptation included utilization of a widely-accepted and recognized laboratory technique of electrochemical impedance spectroscopy (EIS) for the investigation of coating deterioration and substrate corrosion. One of the largest distinctions between the present invention and the prior art is that the present invention allows moisture detection and monitoring of conductive and nonconductive composites with no metal substrate and of adhesives sandwiched between two adherends.

The foregoing objectives can be accomplished utilizing the present invention as a nondestructive moisture-sensing and monitoring device providing an in situ sensor for producing an output correlative to an identifiable impedance spectrum (i.e., the impedance magnitude and phase as a function of the frequency of the applied voltage, created utilizing AC Impedance or Electrochemical Impedance Spectroscopy (EIS)). The preferred embodiment of the invention is a portable, hand-held and nondestructive apparatus, comprising a pen-like or pad-like device which consists of two sensor electrodes one of which serves both as a counter and reference electrode; the other serves as the working electrode. Alternatively, the sensor electrodes may be permanently attached to the structure. The location of the probe electrodes determines what portion of the composite or bonded material is available for inspection. This two electrode sensing device is responsive to water uptake, incubation, hydration and corrosion, which measures differences in impedance spectra; utilizing, one sensor electrode as the counter and reference electrode and the other as the working electrode, applying a small electrical voltage between the two electrodes and measuring the resulting current based upon the applied voltage between the electrodes. The portable, hand-held and in situ moisture-detecting and monitoring sensor contemplated in the present invention is pressed against the composite during inspection, either the two electrodes being on the same side of the composite or opposite sides. Alternatively, the two electrodes may be permanently attached to the composite using conductive paint, ink adhesives or other means. For an adhesive bond the sensor electrodes are temporarily pressed or otherwise attached or permanently attached to opposite sides of the bond. The present invention readily detects the early stages of interfacial degradation well before any visual indication of structural degradation or corrosion appears, as well as the ability to detect, quantify and monitor delamination and structural degradation of composites and bonded structures from its earliest stages under both laboratory and field conditions.

DETAILED DESCRIPTION OF THE PREFERRED EMBODIMENTS

The invention provides a portable, hand-held and nondestructive moisture-sensing device, based on the established technique of electrochemical impedance spectroscopy (EIS), for detecting moisture in composites and adhesively bonded structures.

Figure 1:
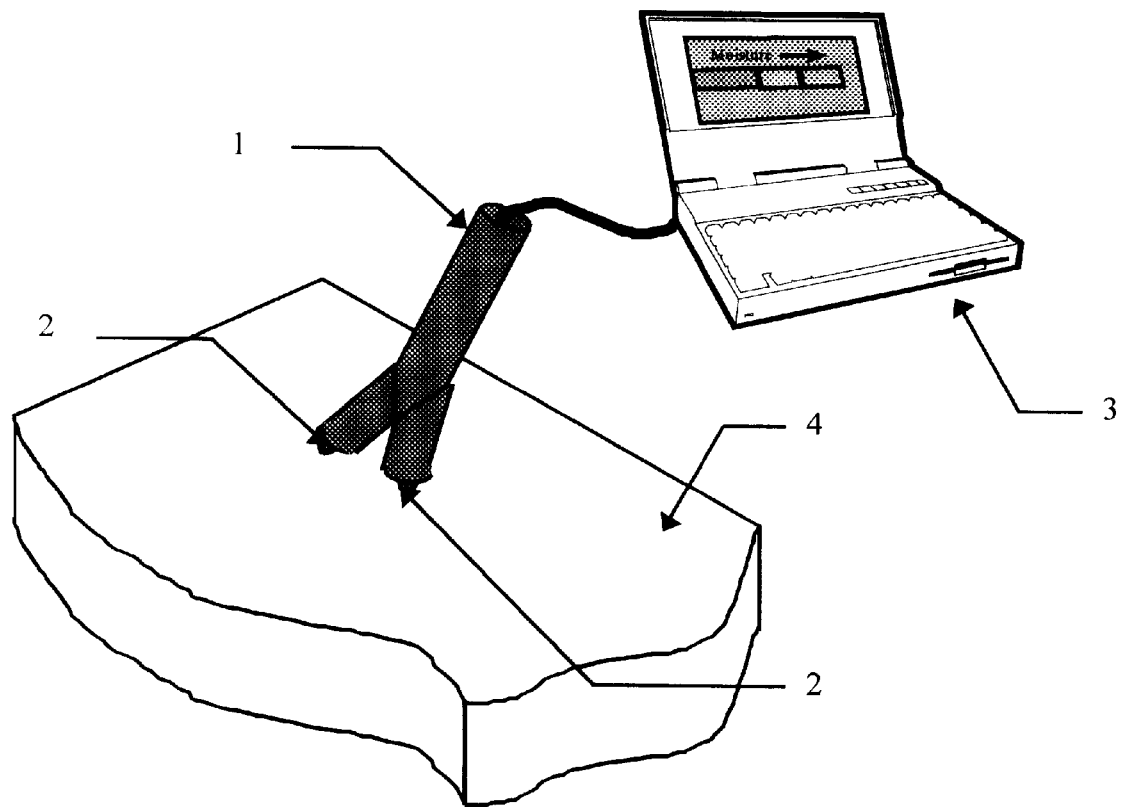
FIG. 1 Prototype moisture sensor (1) showing two electrodes (2) connected to a portable computer (3) which interrogates the composite or adhesively bonded structure (4) and converts the sensor signal to a moisture content.

Referring to the drawings, FIG. 1 is a drawing of the portable hand-held sensor (1) which consists of two electrodes (2, 3) which are pressed against a composite material or adhesively bonded structure (4) for inspection. One electrode serves as both a counter and reference electrode and the other serves as the working electrode. The electrodes can be in a pen-like configuration, a pad-like configuration, or a permanently attached configuration using conductive ink or tape, but are depicted in this Figure in a pen-like configuration. For a composite structure, the electrodes may be placed on the same side of the material or on opposite sides. For an adhesively bonded structure, the electrodes are placed on opposite sides of the adhesive bond. The sensor is attached via cables (5) to a computer-controlled potentiostat (6). The potentiostat applies a small electrical voltage of varying frequencies to the two electrodes and measures the current that is induced by the voltage. The computer uses the voltage and current to generate an impedance spectrum that can be interpreted to indicate the amount of moisture in the composite or adhesive bond. The portion of the structure being inspected depends on the electrical conductivity of the material and the material's surface. A metallic or conductive composite structure, such as graphite-epoxy, will allow moisture to be detected over a large area. The electrodes will detect moisture in a nonconductive composite or bonded structure in a small area near the electrodes unless the surface is wet, allowing the signal to propagate over the wetted area. In these cases, the wetted area can be used to define the area being inspected.

Figure 2:
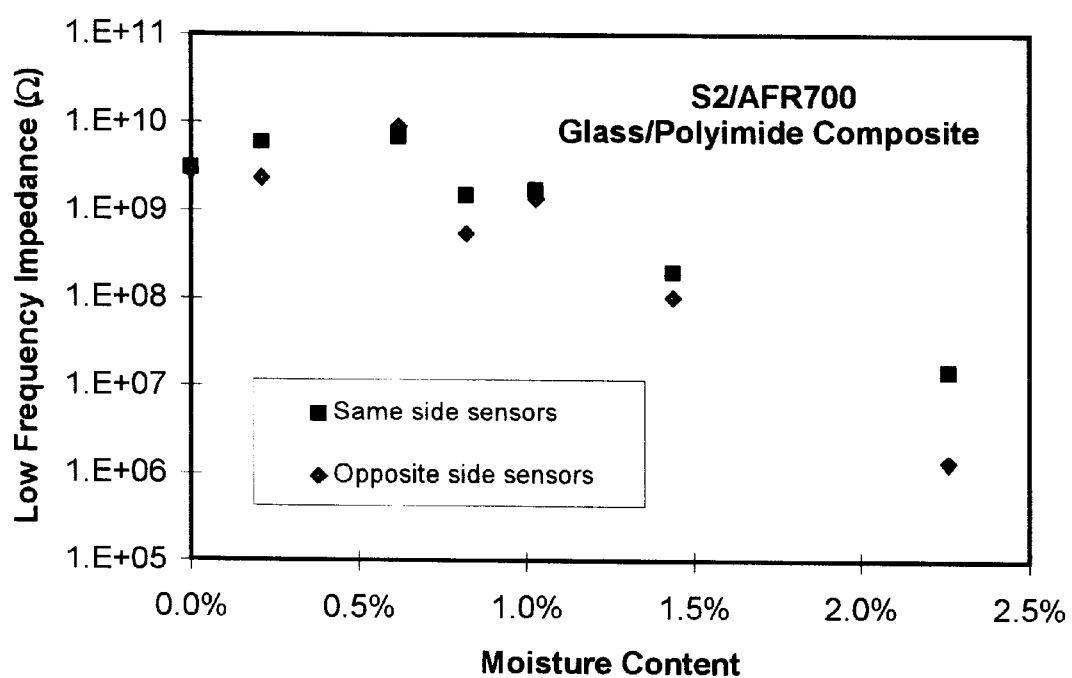
FIG. 2 Sensor signal as a function of moisture content for a glass/polyamide composite.
Figure 3:
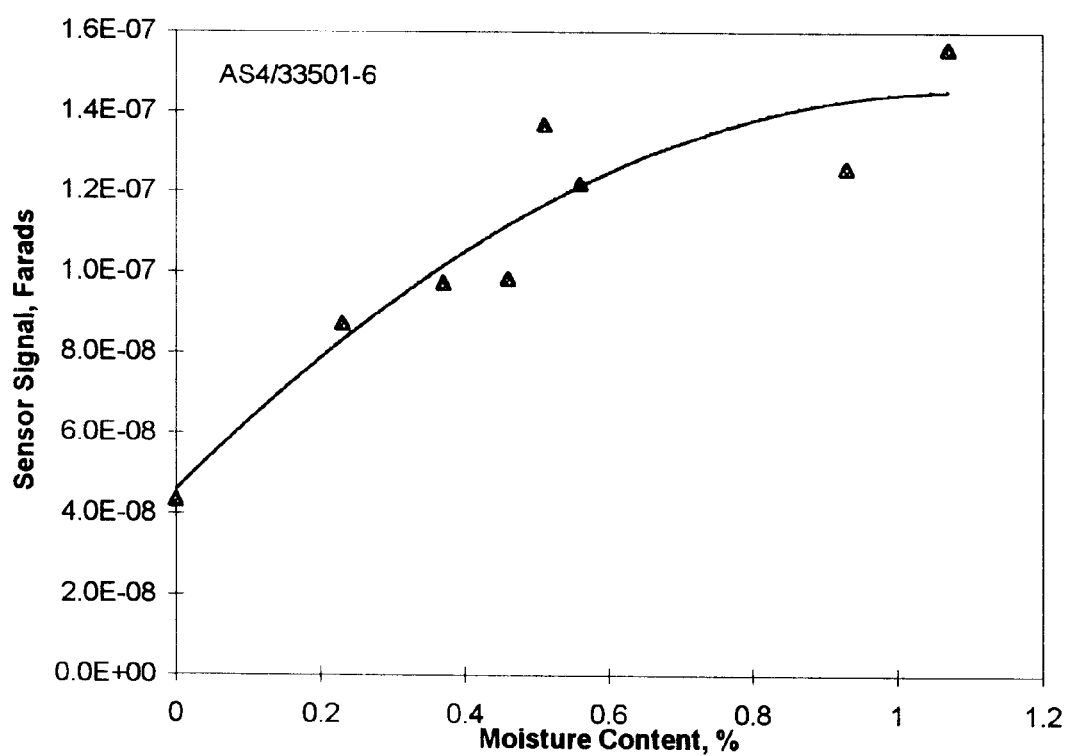
FIG. 3 Sensor signal as a function of moisture content for graphite/epoxy composite.
Figure 4:
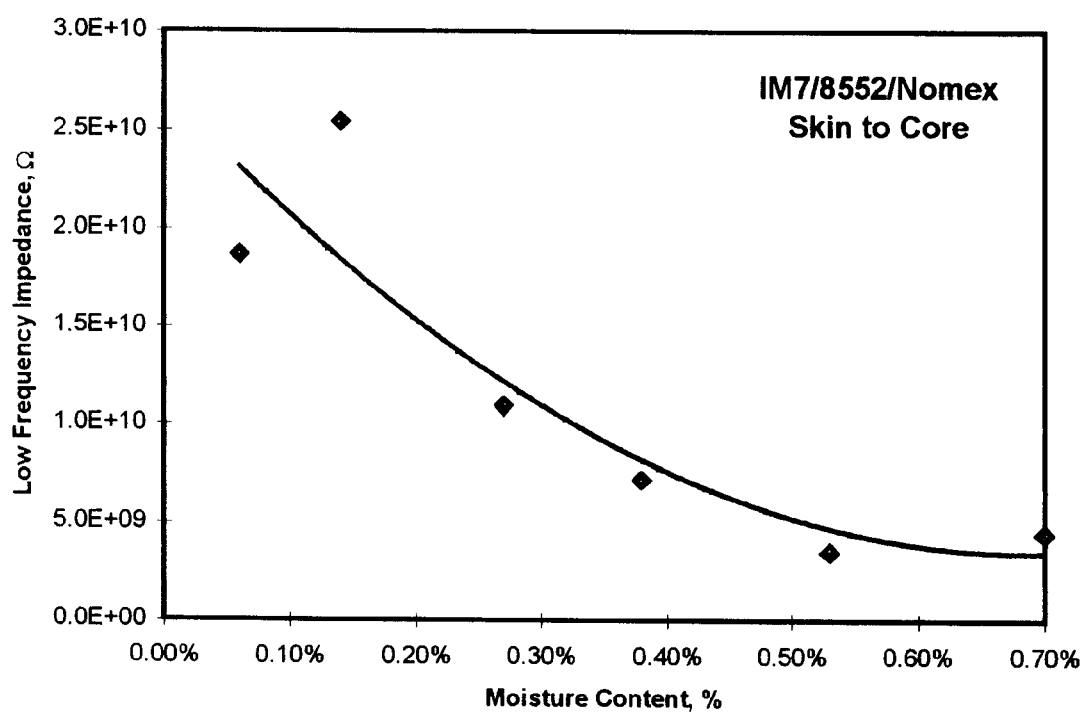
FIG. 4 Sensor signal as a function of moisture content for a graphite/epoxy/honeycomb bonded structure.
Figure 5:
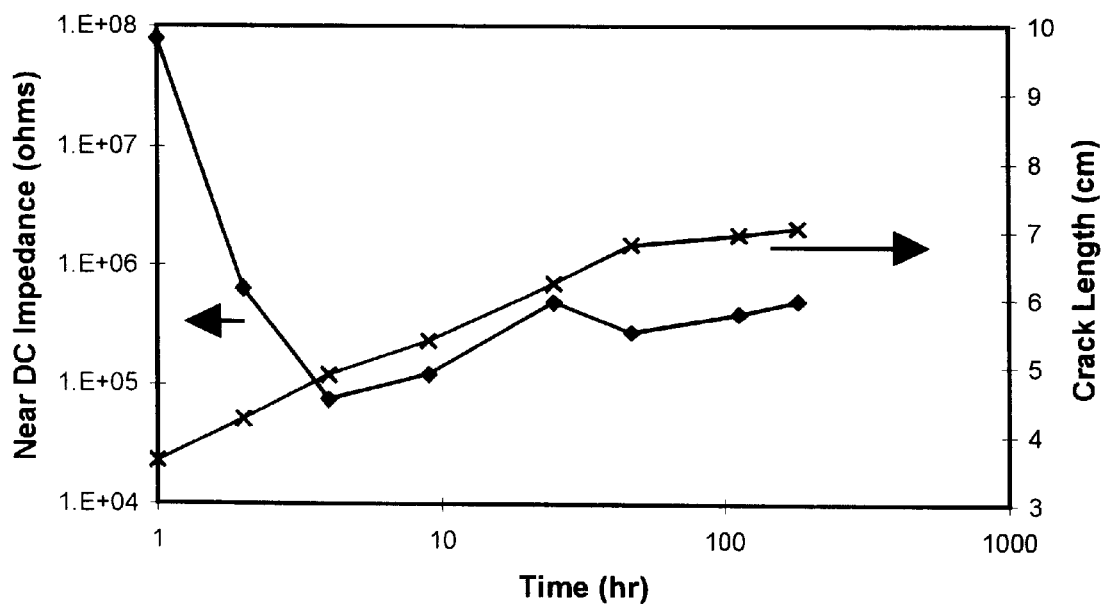
FIG. 5 Sensor signal as a function of time for a double cantilever beam adhesively bonded specimen. The signal reflects the uptake of moisture during the test and the slow decrease in moisture at the crack tip as the crack propagates.

Moisture content of the composite or adhesively bonded structure can be determined from the EIS impedance spectra based on calibration curves (FIGS. 2, 3, and 4), which may depend on the particular composite material being inspected. Data analysis may be as simple as using the impedance at a given low frequency or an average over a range of frequencies. For the example given in FIG. 2, a low-frequency impedance of 1E8 Ω would correspond to a moisture content of ~1.5%. Alternatively, equivalent circuit analysis or other more detailed analysis may be needed, especially when conductive composites, such as graphite-epoxy, are being inspected. In the example given in FIG. 3, an equivalent circuit analysis providing a capacitance of 1E-7 F. would correspond to a moisture content of ~0.4%. This more detailed analysis is likely to give more reliable results than relying on a small number of points and may provide more information, such as the bonded area and bond thickness of an adhesively bonded structure. In the example given in FIG. 5, the crack length or delaminated (debonded) area (obtained by multiplying the crack length by the bond width) of the adhesive bond is shown to correspond to the low-frequency (near DC) impedance after ~3 hours of exposure to moisture.

We claim:

1. A method detecting moisture absorption, electrochemical corrosion, and adhesive bond degradation in composite laminations, honeycomb, and adhesively bonded structures comprising steps of:
    (a) providing a sensor consisting of a first and a second electrode, said first and second-electrode are pressed against a specific material; simultaneously an electrical voltage is applied to that material to produce an electrical output correlating to an identifiable impedance spectrum of that specific material; said first and second electrode serving as a reference and a working electrode responsive to water uptake, incubation, hydration, and corrosion to produce differences in impedance spectra, thus eliminating the need for electrolyte immersion of the composite laminations or honeycomb or adhesively bonded structures being tested;

(b) utilizing the first electrode of the sensor as a counter reference and a second electrode as a working electrode, and pressing electrodes against the top of said material; applying a small electrical voltage between the two electrodes; and measuring the resulting current based upon the applied voltage between the electrodes;

(c) converting an analog signal indicative of the measured current to a corresponding ac impedance signal; and (d) converting the impedance spectrum as a function of accelerated exposure and interpreting said spectrum as a functional expression which correlates to distinctive impedance spectra that are material specific, in order to determine the amount of moisture uptake or the stage of corrosion to that said material has experienced.

2. The method according to claim 1, wherein said sensor is used to detect and evaluate corrosion or coating degradation of the material by wetting the surface of said material with water or other electrolyte.

* * * * *